United States Patent
Pistrol et al.

(10) Patent No.: US 10,435,852 B2
(45) Date of Patent: Oct. 8, 2019

(54) METHOD FOR DETERMINING THE COMPACTION STATE OF SUBSTRATE

(71) Applicant: Hamm AG, Tirschenreuth (DE)

(72) Inventors: Johannes Pistrol, Mödling (AT); Fritz Kopf, Vienna (AT); Werner Völkel, Neustadt (DE); Sebastian Villwock, Pechbrunn (DE)

(73) Assignee: Hamm AG, Tirschenreuth (DE)

( * ) Notice: Subject to any disclaimer, the term of this patent is extended or adjusted under 35 U.S.C. 154(b) by 226 days.

(21) Appl. No.: 15/366,303

(22) Filed: Dec. 1, 2016

(65) Prior Publication Data
US 2017/0159246 A1 Jun. 8, 2017

(30) Foreign Application Priority Data
Dec. 2, 2015 (DE) .................. 10 2015 120 874

(51) Int. Cl.
*E01C 19/28* (2006.01)
*G01N 3/32* (2006.01)
*G01N 9/00* (2006.01)

(52) U.S. Cl.
CPC ............. *E01C 19/288* (2013.01); *G01N 3/32* (2013.01); *G01N 9/00* (2013.01); *E01C 19/286* (2013.01)

(58) Field of Classification Search
CPC .. G01N 3/08; G01N 3/32; G01N 9/00; G01N 9/002; E01C 19/28; E01C 19/286; E01C 19/288

(Continued)

(56) References Cited

U.S. PATENT DOCUMENTS

| 3,599,543 A | 8/1971 | Kerridge |
| 5,797,699 A * | 8/1998 | Blancke ............... E01C 19/288 404/117 |

(Continued)

FOREIGN PATENT DOCUMENTS

| DE | 2007448 | 9/1970 |
| DE | 3707648 | 2/1996 |

(Continued)

OTHER PUBLICATIONS

European Search Report of EP 16200911 or 16 20 0911 dated May 2, 2017, 7 pages.

(Continued)

*Primary Examiner* — Benjamin R Schmitt
(74) *Attorney, Agent, or Firm* — Rankin, Hill & Clark LLP

(57) ABSTRACT

A method for determining the compaction state of a subgrade to be compacted using a roller compactor comprising at least one compactor drum having an oscillation-inducing arrangement and rotatable about a drum axis of rotation comprising the following steps: during at least one period of oscillating movement of the compactor drum, repeatedly determining the acceleration of the compactor drum in an first direction, representing a first acceleration value; in association with each first acceleration value, determining an acceleration of the compactor drum in a second direction representing a second acceleration value in order to provide acceleration value pairs, each consisting of a first acceleration value and a second associated acceleration value; and for at least one oscillation period, defining a compaction state value representing the compaction state of the subgrade based upon the period of oscillation determined for said acceleration value pairs.

9 Claims, 3 Drawing Sheets

(58) Field of Classification Search
USPC .............................. 73/32 R, 32 A, 662, 672
See application file for complete search history.

(56) References Cited

U.S. PATENT DOCUMENTS

| | | | |
|---|---|---|---|
| 7,669,458 B2 | 3/2010 | Commuri et al. | |
| 2014/0341650 A1* | 11/2014 | Villwock | ................ E02D 3/026 404/117 |
| 2015/0211199 A1 | 7/2015 | Corcoran et al. | |

FOREIGN PATENT DOCUMENTS

| | | |
|---|---|---|
| DE | 3590610 | 9/1997 |
| EP | 0053598 | 6/1982 |
| GB | 1224123 | 3/1971 |
| JP | H08-105011 | 4/1996 |
| JP | 2003-193416 | 7/2003 |
| JP | 2008-050859 | 3/2008 |
| WO | 1995/010664 | 4/1995 |

OTHER PUBLICATIONS

Search Report of DE Application No. 102015120874.1 dated Oct. 13, 2016, 8 pages.

\* cited by examiner

METHOD FOR DETERMINING THE COMPACTION STATE OF SUBSTRATE

BACKGROUND

The present invention relates to a method for determining the compaction state of a subgrade to be compacted by means of a roller compactor having at least one compactor drum rotatable about an axis of rotation.

In order to compact a subgrade such as for the application of pavement in road construction, roller compactors are used which, using the weight of their footprint exerted in an essentially vertical direction by one or more compactor drums, enable the compression of the subgrade and, consequently, an increase in the degree of compaction. In order to improve the compaction result, it is known to associate one or more compactor drums of a roller compactor with an oscillation-inducing arrangement, which, due to the generation of periodically oscillating torque, the compactor drum will be put into a corresponding periodic oscillating motion or rather oscillating rotation, meaning an alternating reciprocal motion around the rotational axis of the drum. Given the rotational motion of the compactor drum inherently present with the forward motion of the roller compactor, this oscillating rotation of the compactor drum will be transferred to the rotational axis of the compactor drum.

From DE 35 90 610 C2, the deduction of a degree of compaction is known given the progress over time of the oscillating torque generated in a compactor drum created by the generation of an oscillating rotation, specifically the measured horizontal acceleration of the compactor drum's axis.

DE 37 07 684 C2 discloses a method for determining the degree of compaction of a subgrade to be compacted using a compactor drum. This method measures the vertical acceleration of a compactor drum set into vertically vibrating motion by a vibrating arrangement. Since the vertical movement of the compactor drum changes as the level of compaction increases, the trend in the vertical acceleration of the compactor drum can be used to provide an indication of the compaction state of a subgrade to be compacted.

BRIEF DESCRIPTION

It is the object of the present invention to provide a method for determining the compaction state of a subgrade, which, using simple means, allows for the ability to determine the exact compaction state of a subgrade to be compacted during the performance of the compaction process.

This problem will be solved by a method according to the invention for determining the compaction state of a subgrade to be compacted using a roller compactor comprising at least one compactor drum rotatable about a drum axis of rotation, whereby at least one drum of said roller compactor is associated with an oscillation-inducing arrangement for inducing an oscillating rotation in said compactor drum in order to generate an oscillating torque on the drum axis of rotation, whereby the method comprises the following steps:
  a) during at least one period of oscillating movement of the compactor drum, repeatedly determining the acceleration of the compactor drum in a first direction, representing a first acceleration value,
  b) in association with each first acceleration value, determining the acceleration of the compactor drum in a second direction representing a second acceleration value in order to provide pairs of acceleration values, each consisting of a first acceleration value and an associated second acceleration value,
  c) for at least one oscillation period, defining a compaction state value representing the compaction state of the subgrade based upon the period of oscillation determined for said acceleration value pairs.

The present invention is based upon the knowledge that, during the performance of the compaction process by means of a rotary oscillation being induced in the compactor drum due in turn to the influence of the oscillating rotation transferred as a result of the rolling motion of the compactor drum, said compactor drum will move within the depression that it has itself created in an up-and-down motion, meaning that it will accelerate in a vertical direction which is essentially at a right angle to the surface of the subgrade to be compacted. This results in a periodic change in the vertical acceleration of the compactor drum, whereby the frequency of the vertical acceleration or rather the vertical motion is equal to twice the frequency of the oscillating motion. Given the acceleration value pairs generated during a particular period of oscillation, which, as a whole, reflect the trend of the acceleration in both directions during said oscillation period, the compaction state of a subgrade to be compacted can be deduced.

In the method according to the invention, it is advantageously provided that step c) for determining the compaction condition value will comprise the area of a curve defined by consecutive plots of acceleration value pairs on a graph of acceleration values during an oscillation period, whereby the acceleration value graph is defined by a first graph axis associated with the first acceleration values and a second graph axis associated with the second acceleration values. Since the extent of the acceleration in the horizontal direction is primarily determined by the oscillating torque exerted upon the compactor drum, while the vertical acceleration primarily depends upon how firm the subgrade is and how strongly the compactor drum is pressing into the subgrade to be compacted, thereby moving up and down during the course of an oscillating motion, the plot of acceleration value pairs recorded during an oscillation period represents an area whose size depends upon the compaction state of the subgrade.

The first direction advantageously corresponds to a generally horizontal direction and the second direction advantageously corresponds to a generally vertical direction. It should be pointed out here that, in terms of the present invention, the horizontal direction can be regarded as a direction generally parallel to the plane of the surface to be compacted, while the vertical direction can be regarded as the direction generally orthogonal to said plane of the surface or subgrade to be compacted.

In order to be able to determine the extent of the area encompassed by the plotted pairs of acceleration values using simple mathematical means, the method according to the invention may additionally provide that, regarding step c):
  an acceleration value pair vibration will be defined based upon a sequence of acceleration value pairs along the first axis of the graph, whereby acceleration value pairs from a first group of acceleration value pairs and a second group of acceleration value pairs will be assigned in such a way that the acceleration value pairs from the first group will generally represent the upper end of the acceleration value pair vibration curve, and the acceleration value pairs from the second group will generally represent the lower end of the acceleration value pair vibration curve.

based upon the first group of acceleration value pairs, an upper envelope is determined, and, based on the second group of acceleration value pairs, a lower envelope is determined, the area value will generally be defined as being the area bordered by the upper envelope and the lower envelope.

BRIEF DESCRIPTION OF THE DRAWINGS

The present invention is described hereinafter in reference to the enclosed drawings. Shown are.

DETAILED DESCRIPTION

Figure 1:
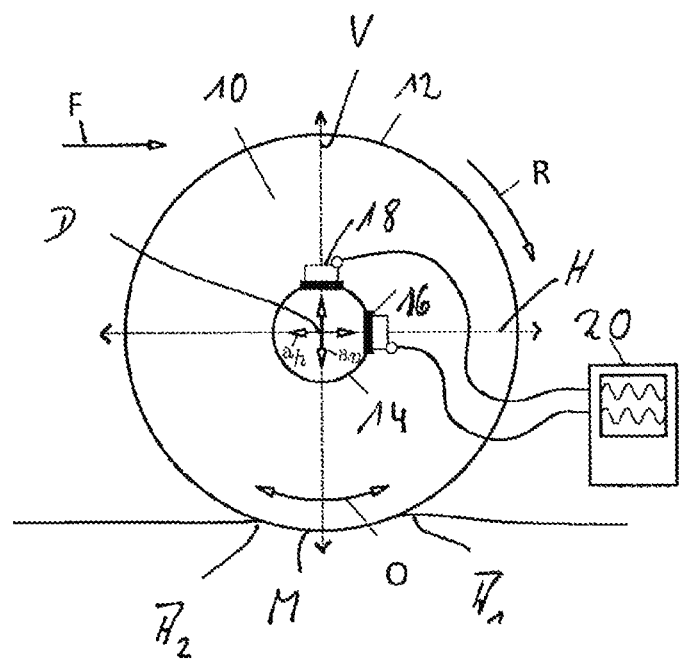
FIG. 1 a side view and figurative representation of the surface to be compacted by a compactor drum.

FIG. 1 shows a side view and figurative representation of a compactor drum 10 of a roller compactor. Provided within the area of the compactor drum 10 enclosed by the drum mantle 12 is an oscillation-inducing arrangement (not visible in the Figures), which may comprise a plurality of axes parallel to the compactor drum for the rotation of eccentric masses driven around an axis of rotation D. By means of the oscillation-inducing arrangement, an oscillating torque is generated, which induces the compactor drum 10 to perform an oscillating rotation O around the axis of rotation D. During the compaction process, meaning during the forward motion of the roller compactor in the direction of travel F, this oscillating rotation in the rolling motion of the compactor drum 10 is transferred along the rolling direction R.

By way of example, acceleration sensors 16, 18 may be provided in the area of a bearing shell 14 of the compactor drum 10. In doing so, the acceleration sensor 16 for registering the acceleration of the compactor drum 10 in a horizontal direction H may be of such design that it lies along a direction substantially parallel to the plane of the subgrade U to be compacted. The acceleration sensor 18 may be designed or arranged in order to detect a vertical acceleration $a_v$ meaning an acceleration in a vertical direction V, which is substantially orthogonal to the horizontal direction H and thus also orthogonal to the subgrade to be compacted. The output signals provided by the two acceleration sensors 16, 18 can be transmitted to a data acquisition/analysis unit 20.

It should be pointed out here that the acceleration may also take place in other areas of the compactor drum 10 such as the interior of the drum mantle 12, which would then require the respective extrapolation of the horizontal or vertical acceleration through coordinate transformation.

The horizontal acceleration $a_h$ and the vertical acceleration $a_v$ will be recorded repeatedly during a particular period of oscillating movement O. The sampling rate should be at least ten times that of the oscillation frequency of the compactor drum 10, so that, during each period of oscillating movement O, at least ten acceleration value pairs will be recorded or determined, each with a horizontal acceleration $a_h$ representing a first acceleration value and a vertical acceleration value $a_v$ representing a second acceleration value. In the process, both acceleration values in a respective pair of acceleration values are ideally values for vertical acceleration and horizontal acceleration recorded at the same time.

During the rolling motion atop the subgrade U to be compacted, a discernible depression M forms beneath the compactor drum 10 in FIG. 1, which is restricted both toward the direction of travel F and opposite to the direction of travel F through the respective accumulations of material $A_1$ and $A_2$. In the course of the oscillating movement of the compactor drum 10, said compactor drum 10 oscillates back and forth within the depression M and, in so doing, experiences not only the acceleration generated by the oscillating torque in a horizontal direction H, but also by the periodic rolling onto and off of the accumulations of material $A_1$ and $A_2$, therefore an acceleration in the vertical direction V. During each period of oscillation, the compactor drum 10 is moved by each of the two accumulations of material $A_1$ and $A_2$, once up and once down, so that the frequency of the vertical acceleration is double the frequency of the horizontal acceleration.

Figure 2:
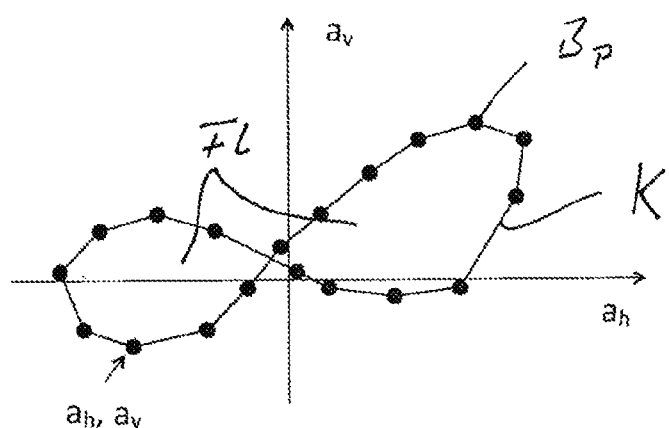
FIG. 2 a graph of the period of oscillation of a compactor drum as shown in FIG. 1 showing a number of acceleration value pairs determined therein, and an acceleration value pair curve spanning the acceleration pair values as determined in chronological order.

FIG. 2 shows a graph or coordinate system, in which the first acceleration value, meaning the horizontal acceleration $a_h$, is assigned to the horizontal axis, and the second acceleration value, meaning the vertical acceleration $a_v$, is assigned to the vertical axis. FIG. 2 shows a plurality of the respective acceleration value pairs $B_P$, wherein each acceleration value pair $B_P$ is represented by a horizontal acceleration value $a_h$ and an associated vertical acceleration value $a_v$ recorded at essentially the same time. FIG. 2 shows acceleration value pairs $B_P$ for one period of oscillating movement O of the compactor drum 10. The sequence of the acceleration value pairs $B_P$ over time, which are determined or recorded in chronological order, defines an acceleration value pair curve K, the shape of which generally resembles that of an "8" on its side. This shape is due to the fact that, as was previously set out, two periods of vertical acceleration occur during a period of oscillating movement O, meaning between the two extremes of the horizontal acceleration value $a_h$, so the sign for the vertical acceleration changes a total of four times.

During the process of compaction, the degree of compaction of the subgrade to be compacted U gradually increases with the number of passes by the roller compactor. Given increasing compaction, the extent to which the compactor drum 10 can press into the subgrade U decreases, which corresponds to a decrease in the depth of the depression M and a decrease in the amount of the accumulations of material $A_1$ and $A_2$. Given the decrease in the depth of the depression and the amount of the accumulations of material $A_1$ and $A_2$, the firmness of the subgrade U increases. Not only the depth of the depression M and the amount of the accumulations of material $A_1$ and $A_2$ but also the firmness of the ground upon which the compactor drum 10 performs its oscillating movement O will affect the values for horizontal acceleration $a_h$ and vertical acceleration $a_v$ occurring during a particular period of oscillating movement O. It was determined that the area defined by the acceleration values pair curve K likewise increases with an increasing degree of firmness, specifically because the horizontal acceleration $a_h$ increases as the firmness of the subgrade increases, thus making the sideways "8" wider. Taking the acceleration value pairs determined during a particular period of oscillating movement O into account, it thus becomes possible to draw conclusions about the subgrade U to be compacted, specifically by determining the size of the area defined by the acceleration value pairs $B_P$ or the acceleration value pair curve K in the acceleration pair graph in FIG. 2.

Figure 3:
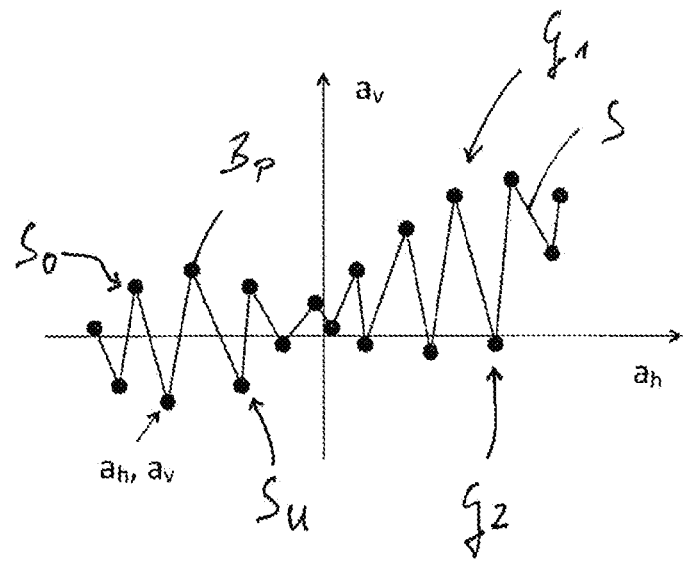
FIG. 3 a graph corresponding to that of FIG. 2, in which the acceleration value pairs determined for the period of oscillation are arranged in a different way in order clarify the acceleration value pair vibration.

There are various ways of determining this area. For example, instead of arranging or combining the acceleration value pairs $B_P$ one after the other in chronological order in order to obtain the acceleration pair curve K shown in FIG. 2, one may rather select, for instance, alternating acceleration value pairs beginning with the smallest value for horizontal acceleration $a_h$, which will form a local minimum or maximum, in order to define a fictional acceleration value pair vibration S, as is illustrated in FIG. 3. In the process, for example, one might proceed by utilizing a corresponding sequence of acceleration pairs $B_P$ alternating with an acceleration value pair $B_P$ for defining a local minimum, being a lower end $S_U$, and a local maximum, being an upper end $S_O$. For example, if the chronological sequence of the provided acceleration value pairs $B_P$ should result in a grouping, within which two or more acceleration value pairs, each defining a lower end point, are located between two upper end points $S_O$, then that acceleration value pair $B_P$, which in fact defines the local minimum or, as the case may be, the local maximum, can be utilized for the purpose of determining the acceleration value pair vibration S.

As a whole, the acceleration value pairs which define the acceleration value pair vibration S are to be divided into two groups, namely one group $G_1$, which includes the acceleration value pairs $B_P$ defining the respective upper end $S_O$, and a second group $G_2$, which includes the acceleration value pairs $B_P$ defining the lower end $S_U$. In the process, the two outermost horizontal acceleration values may advantageously be assigned to groups $G_1$ and $G_2$, respectively.

On the basis of the respective acceleration value pairs $B_P$ assigned to each of the groups $G_1$ and $G_2$, appropriate mathematical methods are used to determine an upper envelope $E_O$ and a lower envelope $E_U$ for the acceleration value pair vibration S.

As determined according to the invention, the size of the area FL, which is an indicator of the compaction state of the subgrade U to be compacted, can now be calculated as the area enclosed between both ends of the envelope $E_O$ and $E_U$. In doing so, for example, an area calculation can be made through numerical integration using the trapezoidal rule. The area value, the unit for which is $m^2/s^4$, thus constitutes a compaction control value, meaning a dynamic continuous compaction control value, which may be recorded or determined during the compaction process. As an example, this value may be rescaled along with compaction process parameters or machine parameters such as the compactor drum diameter, the linear load on the vibrating mass itself, or the eccentric moment in order to obtain variables which are easily manageable or more comparable.

Figure 5:
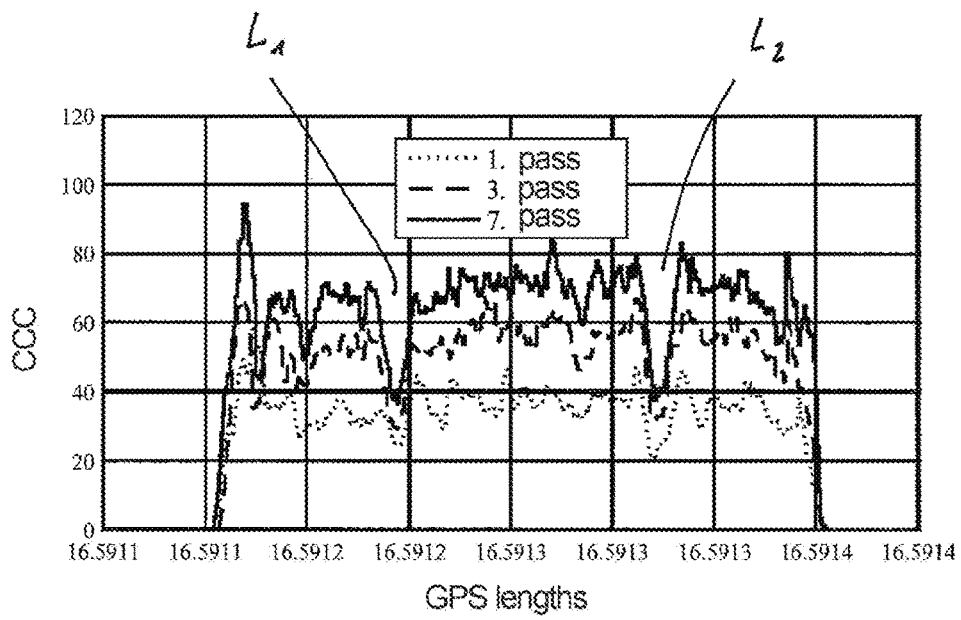
FIG. 5 the progress of a compaction state value determined by the method according to the invention following an increasing number of passes over a subgrade to be compacted.

FIG. 5, given the length of a subgrade U to be compacted as represented by lengthwise GPS areas, shows the progress of the area size FL as determined in the manner described in the foregoing, which is indicated in FIG. 5 as FDVK [continuous compaction control], the value for which can be clearly seen to shift continuously upwards with an increasing number of passes. Weak points are present in two local regions $L_1$ and $L_2$, these being places where, for reasons such as a lack of subgrade preparation, no substantial compression may be achieved.

Figure 6:
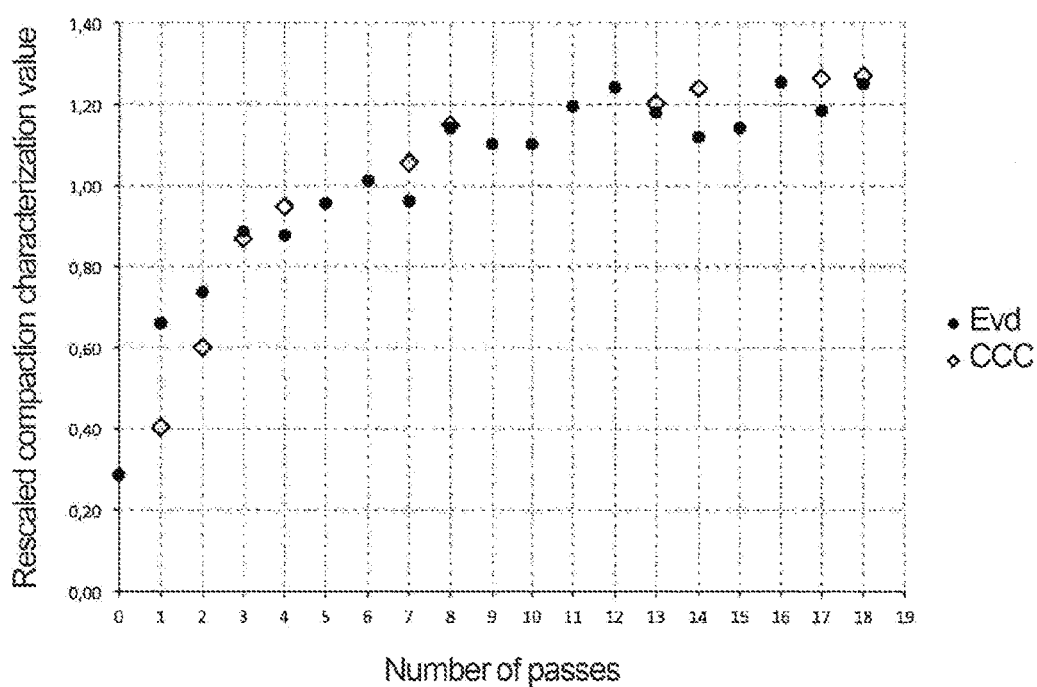
FIG. 6 plotted with respect to the number of passes, the progress of a compaction state value determined by the method according to the invention, as well as a degree of compaction determined by measurements made at the subgrade.

FIG. 6 shows a comparison between the FDVK [continuous compaction control] area value recorded using the method according to the invention and a value determined using a standardized measurement procedure with a dynamic deformation modulus corresponding to Evd. The progress of these two values proceeds in a nearly comparable manner as the number of crossings increases, thus making it evident that the use of the method according to the invention makes a variable available which allows precise conclusions to be made about the actual degree of compaction existing in the subgrade to be compacted in real time, thus during the compaction process.

Figure 4:
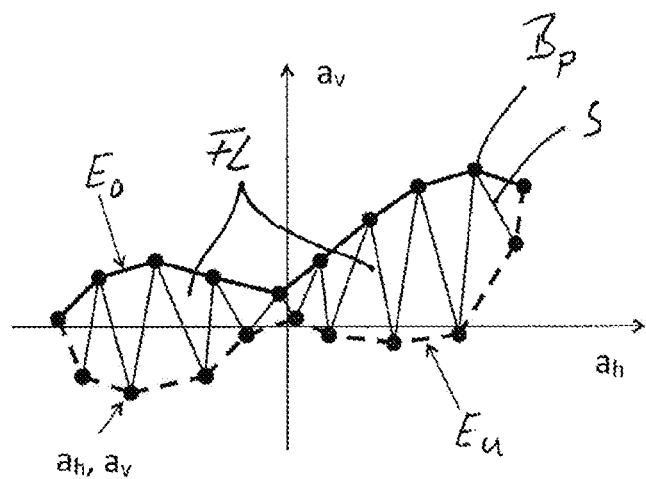
FIG. 4 a graph, which, based on the arrangement of the acceleration value pairs according to FIG. 3, shows an upper envelope and a lower envelope for the acceleration value pair vibration.

Finally, it should be pointed out that, as regards the foregoing reference to the graphs or coordinate systems in FIGS. 2 to 4 and the acceleration value pairs or curves entered therein, the determination of the area value does not, in fact, require entering the respective acceleration values or acceleration value pairs into graphs and evaluating said graphs, but is instead carried out on the basis of mathematical procedures, which, however, are able to be shown via the various graphs and the curves entered therein. Therefore, in terms of the present invention, for example, this does not mean that an acceleration value pair vibration will be plotted on a graph—or merely plotted on a graph—in the process of defining such an acceleration value pair vibration, but rather that values or coordinate points relevant to said vibration will be determined and utilized in further mathematical procedures.

The invention claimed is:

1. A method for determining the compaction state of a subgrade to be compacted using a roller compactor comprising at least one compactor drum rotatable about a drum axis of rotation, wherein one of the at least one compactor drum of the roller compactor is associated with an oscillation-inducing arrangement for inducing an oscillating rotation in said compactor drum in order to generate an oscillating torque on the drum axis of rotation, wherein the method comprises the following step:
    a) during at least one period of oscillating movement of the compactor drum, repeatedly determining the acceleration of the compactor drum in a horizontal direction, representing a first acceleration value,
    b) in association with each first acceleration value, determining an acceleration of the compactor drum in a vertical direction representing a second acceleration value in order to provide acceleration value pairs, each consisting of one of the first acceleration values and the associated second acceleration value, and
    c) for at least one period of oscillation, defining a compaction state value representing the compaction state of the subgrade based upon the period of oscillation determined for said acceleration value pairs,
    wherein step c) for determining the compaction state value comprises determining the area of an acceleration value pair curve defined by consecutive plots of acceleration value pairs on a graph of acceleration values during one period of oscillation, wherein the acceleration value graph is defined by a first graph axis associated with the first acceleration values and a second graph axis associated with the second acceleration values.

2. The method according to claim 1, wherein, regarding step c), an acceleration value pair vibration is defined based upon a sequence of acceleration value pairs along the first graph axis.

3. The method according to claim 2, wherein acceleration value pairs from a first group of acceleration value pairs and a second group of acceleration value pairs are assigned in such a way that the acceleration value pairs from the first group of acceleration value pairs generally form the upper end of the acceleration value pair vibration and the acceleration value pairs from the second group of acceleration value pairs generally form the lower end of the acceleration value pair vibration.

4. The method according to claim 3, wherein, regarding step c), an upper envelope is determined based upon the first group of acceleration value pairs, and a lower envelope is determined based upon the second group of acceleration value pairs.

5. The method according to claim 4, wherein, regarding step c), the area value is generally defined as being the area bordered by the upper envelope and the lower envelope.

6. The method according to claim 1, wherein during a rolling motion of the roller compactor, a depression forms beneath said compactor drum, wherein the depression is restricted toward a direction of travel and opposite to the direction of travel through accumulations of material.

7. The method according to claim 6, wherein the said compactor drum oscillates back and forth within the depression and, during each period of oscillation, the compactor drum is moved once up and once down by each of the accumulations of material.

8. The method according to claim 7, wherein a depth of the depression and an amount of the accumulations of materials gradually decreases by the oscillating rotation in said compactor drum causing the acceleration of the compactor drum in a horizontal direction to increase.

9. The method according to claim 8, wherein a frequency of the second acceleration value is double a frequency of the first acceleration value during each period of oscillation.

* * * * *